United States Patent [19]

Walker et al.

[11] Patent Number: 5,597,384

[45] Date of Patent: Jan. 28, 1997

[54] COLOR CODING FOR IMPLANT SELECTION

[75] Inventors: Michael R. Walker; Timothy R. Miller, both of Warsaw, Ind.

[73] Assignee: Zimmer, Inc., Warsaw, Ind.

[21] Appl. No.: 305,232

[22] Filed: Sep. 13, 1994

[51] Int. Cl.$^6$ ............................................. A61F 2/38
[52] U.S. Cl. ......................... 623/66; 623/18; 623/20; 206/459.5
[58] Field of Search ...................... 623/16–23, 66; 206/459.5

[56] References Cited

U.S. PATENT DOCUMENTS

| | | | |
|---|---|---|---|
| 3,910,412 | 10/1975 | Vargo | 206/459.5 |
| 4,822,366 | 4/1989 | Bolesky | 623/20 |
| 5,031,488 | 7/1991 | Zumeta | 81/180.1 |
| 5,156,626 | 10/1992 | Broderick et al. | 623/22 |
| 5,226,915 | 7/1993 | Bertin | 623/20 |
| 5,228,571 | 7/1993 | Anderson | 206/459.5 |
| 5,354,299 | 10/1994 | Coleman | 606/73 |
| 5,445,272 | 8/1995 | Crisp | 206/459.5 |

OTHER PUBLICATIONS

Johnson & Johnson Orthopaedics – Booklet – P.F.C. Modular Knee System – Lit. No. LCN 086–6000–85 – Rev. Jul. 1991.

Zimmer Inc. Brochure – MG II Total Knee System, Implants and Instrumentation – No date available.

*Primary Examiner*—John G. Weiss
*Assistant Examiner*—Bruce Snow
*Attorney, Agent, or Firm*—Cary R. Reeves

[57] ABSTRACT

A coding scheme associates multiple codes with one or more of the components of a prosthetic implant system in order to indicate the compatibility among the mating components. It is thus possible for operating room personnel to quickly and accurately select components and verify their compatibility.

5 Claims, 3 Drawing Sheets

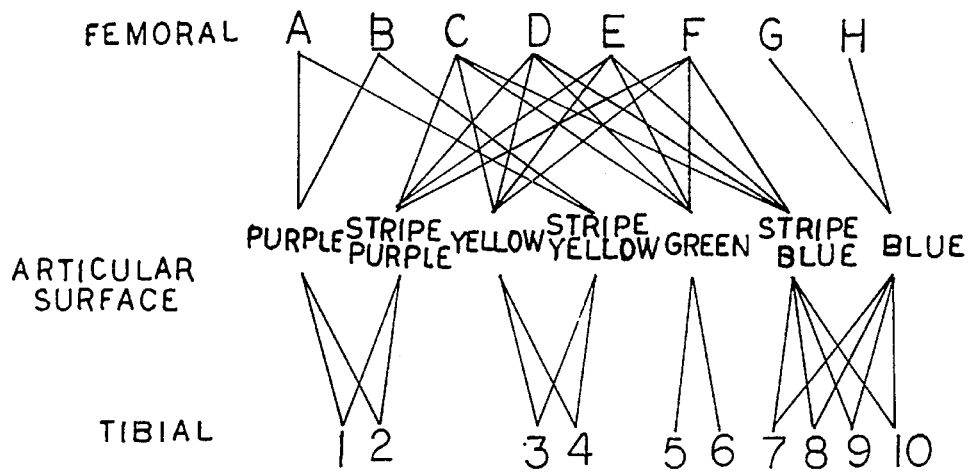
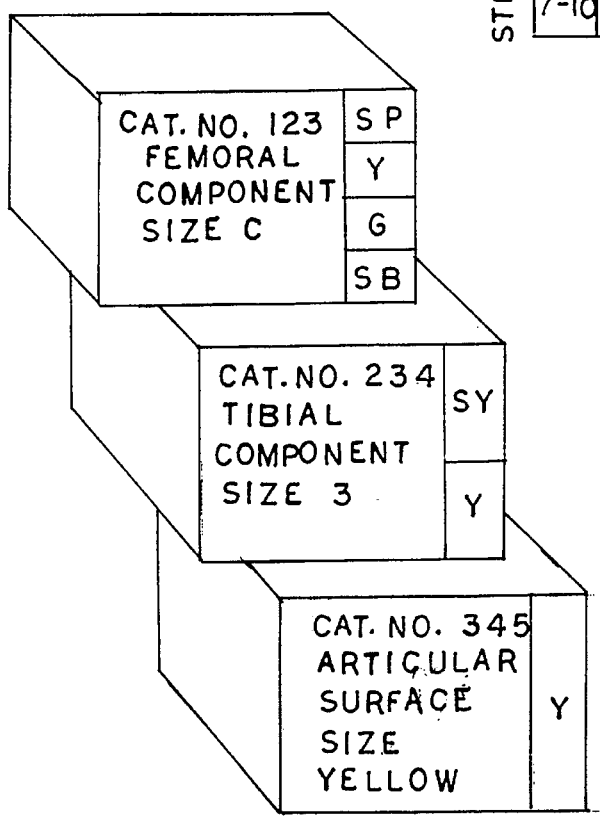
Fig. 6
Fig. 7
Fig. 8

FEMORAL COMPONENT SIZE

| TIBIAL SIZE | SIZE ※1 | SIZE ※2 | SIZE ※3 | SIZE ※4 | SIZE ※5 | SIZE ※6 |
|---|---|---|---|---|---|---|
| SIZE ※1 (X-SMALL) | X | | | | | |
| SIZE ※2 (SMALL) | | X | X | | | |
| SIZE ※3 | | X | X | X | | |
| SIZE ※4 | | | X | X | X | |
| SIZE ※5 | | | | X | X | X |
| SIZE ※6 | | | | | X | X |

"X" DENOTES PROPER COMPATIBILITY

COLOR CODING FOR IMPLANT SELECTION

BACKGROUND OF THE INVENTION

The present invention relates to the use of color coding to facilitate implant selection. More specifically it relates to a color coding scheme that facilitates the proper matching of three components of a modular prosthetic implant system.

Prosthetic implants have been used successfully for many years to replace degenerating or traumatized joints of the human body. Such implants typically comprise a bearing member for each side of the joint. For example, in a knee joint prosthetic implant there is a femoral component for replacing the end of the femur adjacent the knee joint and a tibial component for replacing the end of the tibia adjacent the knee joint. Likewise, in a hip joint prosthetic implant there is an acetabular component for replacing the articular surface of the pelvis and a femoral component for replacing the articular head of the femur. Implants for other joints of the body will have similar components. Each of the two components comprising an implant must attach securely to the underlying supporting tissue, usually bone, on its corresponding side of the joint. Each component must also contain an articular portion for articulating with the other component. However, within the patient population there exist variations in bone size and shape which necessitates a range of sizes of each component so as to have optimal attachment to the underlying support tissue for each patient. The differently sized components may also have differently sized articular regions. In addition, within the patient population there exist different degrees of joint disfunction which require different articular geometries for proper restoration of function.

For example, in a knee joint prosthetic implant, it is desirable for the bottom side of the tibial component to completely cover the resected tibial surface. Proper coverage results in a uniform distribution of forces, takes advantage of the strongest available bone for tibial support, and provides the largest area possible for boney ingrowth into a porous implant. On the other hand, it is important that the tibial component is not so large that it overhangs the edge of the tibia and interferes with the surrounding soft tissues. Similar constraints govern the fit of the femoral component on the resected femur. Once optimal fit of the tibial and femoral components is accomplished, the surgeon must ensure that the femoral and tibial articular surfaces will work together. If the femoral and tibial articular surfaces are not compatible, then the surgeon must alter his size choice for the tibial component or femoral component or both until a set of components that are compatible is selected. More recent knee implant systems have separated the tibial component into a base plate and an articular surface component so that there are three components between the femur and tibia which must be matched for compatibility.

Some implant systems have very limited or specific compatibility between articulating surfaces and mating components such as depicted in FIGS. 1 and 2. FIG. 1 is a cross-reference chart showing the compatibility between femoral and tibial implants. FIG. 2 is a schematic diagram showing with lines drawn between compatible components. Other systems have some flexibility in matching articulating surfaces of mating components. For example, FIG. 3 is a schematic diagram of a system in which any femoral component is compatible with any articular surface component and each articular surface component has two or more compatible tibial plates. In another example, FIGS. 4 and 5 depict an implant system in which there is flexibility in matching femoral components to articular surface components, but there is no flexibility in matching articular surface components and tibial plates.

In order to communicate the compatibility between the various components, systems have used cross-reference charts such as FIGS. 1 and 4 or color codes. The advantage of cross-reference charts is the ability to communicate compatibility of articulating surfaces and mating components for very complex systems in specific terms through the use of catalog numbers or product sizes. The disadvantage of cross-reference charts is that they are slow and cumbersome to use in an environment where speed is important. On the other hand, color coding has the advantage of being able to be used quickly and accurately. However, prior color coding systems have been able to communicate only a limited amount of information and have therefore been limited as to the complexity of the system with which they could be used.

A color coding scheme for a system like the one in FIG. 2 would be redundant with the size information since there is only one-to-one-to-one compatibility. Color coding would serve only to make the size information stand out. In a color coding scheme for this implant system typically a color code would be associated with each of the 5 sizes and each component of a particular size would be marked with the corresponding code. Prior systems have used a single color code on each system. A surgeon could quickly verify compatibility by checking that all of the components selected were the same color code. This is faster and more accurate than reading the sizes.

In a color coding scheme for a system such as the one depicted in FIG. 3, a color is associated with each group of compatible tibial trays and articular components. Each component in the group is marked with a single color code corresponding to the group color. In this system, all of the femoral components are compatible with all of the articular surface components and therefore no color code is associated with the femoral components. Verification of compatibility is accomplished if the selected tibial plate and articular surface have matching color codes.

A more complex implant system with overlapping compatibility between the femoral components and the articular surfaces is shown in FIGS. 4 and 5. Systems such as these have not previously used color coding because of their complexity and the limitations of prior color coding schemes. They have therefore relied solely on cross-reference charts such as FIG. 4.

SUMMARY OF THE INVENTION

The present invention provides a system for color coding implant components having a complex relationship among the various components without the necessity of cross-reference charts. The color coding system of the present invention makes it possible for operating room personnel to quickly and accurately select components and verify their compatibility. The present invention accomplishes these advantages by providing multiple color codes on one or more of the components.

BRIEF DESCRIPTION OF THE DRAWINGS

FIG. 6 is a schematic diagram showing the compatibility between the components of an exemplary knee implant system for demonstrating the present invention.

FIG. 7 is a chart depicting an exemplary coding scheme according to the present invention corresponding to the implant system of FIG. 6.

FIG. 8 is a perspective view of component packaging showing an application of the coding scheme of FIG. 7.

DETAILED DESCRIPTION OF THE INVENTION

Figures 1, 2, 3:
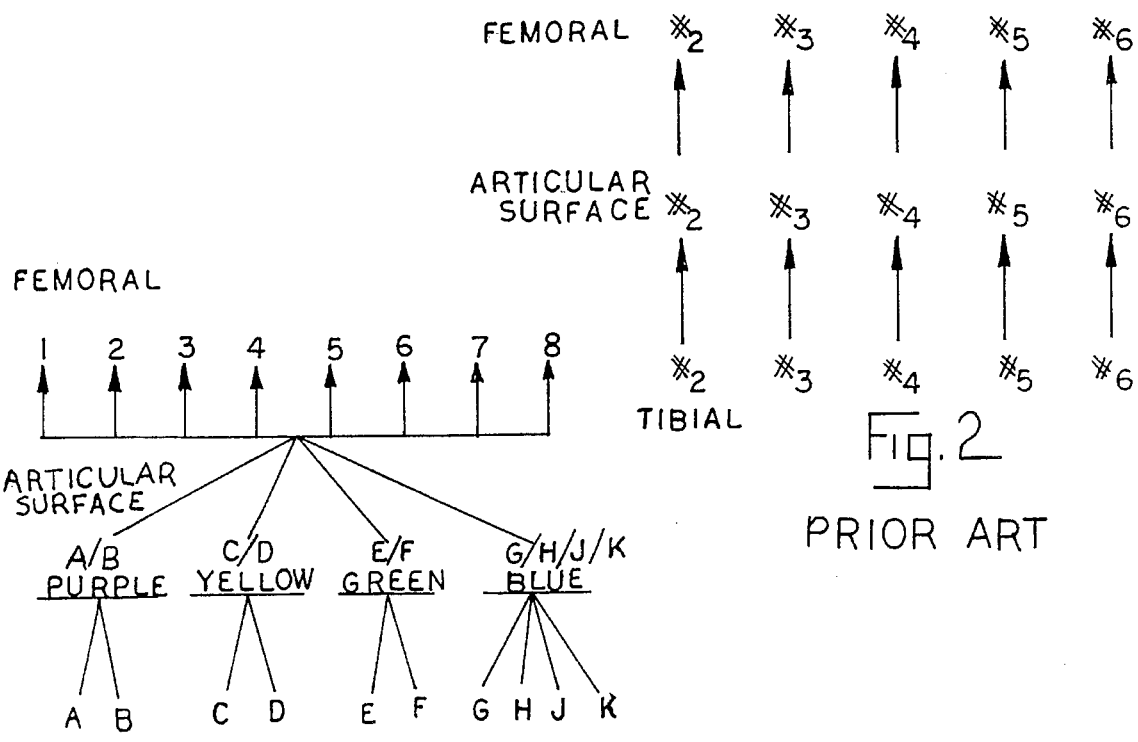
FIG. 1 is a prior art cross-reference chart depicting the compatibility between femoral and tibial components of a knee implant system.
FIG. 2 is a schematic diagram showing the compatibility between the components of the knee implant system of FIG. 1.
FIG. 3 is a schematic diagram showing the compatibility between the components of another prior art knee implant system.
Figures 4, 5:
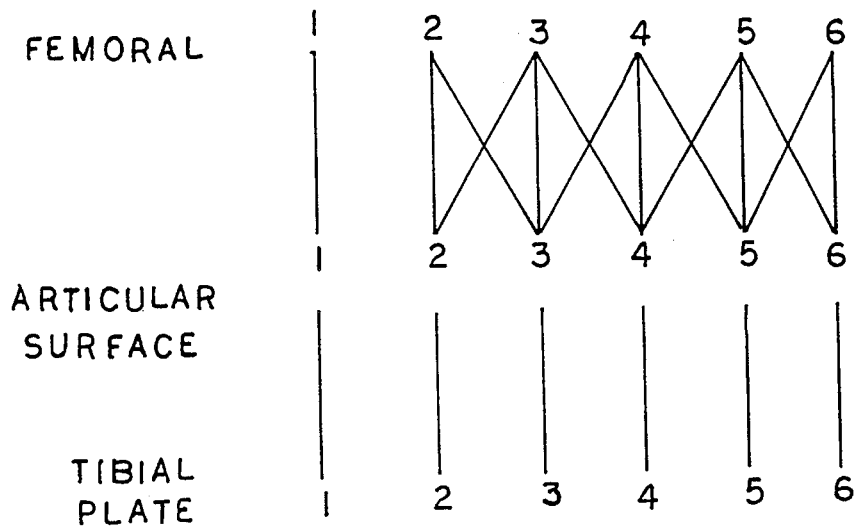
FIG. 4 is a prior art cross-reference chart depicting the compatibility between femoral and tibial components of another prior art knee implant system.
FIG. 5 is a schematic diagram showing the compatibility between the components of the knee implant system of FIG. 4.

FIG. 6 schematically depicts the compatibility between femoral, tibial and articular surface components of an exemplary knee system. In this system the femoral component sizes are designated by the letters A through H and the articular surface component sizes are designated by the numbers 1 through 10. The present invention provides a coding scheme for communicating the compatibility of the femoral and tibial components with articular surface components. In accordance with this invention a code, preferably a visual code such as a color code, is assigned to a particular size articular surface component. The articular surface components of the example in FIG. 6 are designated by the color codes purple (p), striped purple (SP), yellow (Y), striped yellow (SY), green (G), striped blue (SB) and blue (B). Each femoral component which is compatible with the particular size articular surface component is assigned the same code as the articular surface component. Likewise each tibial component which is compatible with the particular size articular component is assigned the same code. FIG. 7 depicts the coding that would be assigned to each component. For example, a size B femoral component is compatible with a P and an SY articular component and would therefore be coded with both a P and an SY. A size C femoral component is compatible with SP, Y, G, and SB articular components and would be correspondingly coded. Likewise, a size 3 tibial component is compatible with an SY and a Y articular component and would be correspondingly coded. FIG. 8 depicts how the color codes would appear on packaging for the size C femoral, size 3 tibial plate and the Y articular surface.

In use, a surgeon would determine which sizes of components would give the best fit on the tibia and femur. The size selection for the tibia is done independently of the size selection for the femur and vice versa. Next, the surgeon would refer to the coding associated with the selected tibia and femur to determine which codes are common to the tibia and femur. The surgeon may then select a compatible articular surface component corresponding to one of the common codes. For example, as shown in FIG. 8, the surgeon may determine that a size C femoral component provides the best fit on the femur and a size 3 tibial components provides the best fit on the tibia. By then comparing the codes on the femoral and tibial components, the surgeon sees that they have a yellow (Y) code in common and therefore a size Y articular surface will be compatible with both the femoral and tibial components.

Only if there are no common codes between the femoral and tibial components selected would the surgeon consider the tibial or femoral size selection with respect to the other one. In this case the surgeon would adjust either the tibial selection or the femoral selection or both until he selected components with overlapping codes from which he could select a compatible articular surface component. For example, the surgeon might determine that a size B femoral and a size 5 tibial were best. A quick check of the codes on the two implants would show that there is no common code and therefore no compatible articular surface for that pair. The surgeon could then choose to go up one size to a C femoral component use a green articular component or he could choose to go down one size to a size 4 tibial component and use a striped yellow articular surface component. Likewise he could adjust both components so that he would use a size C femoral, a size 4 tibial and a size yellow (Y) articular surface.

The coding scheme according to this invention is also useful subsequent to component selection as a quick and accurate verification of component compatibility. For this purpose, a surgeon or other operating room personnel would verify prior to implanting the three components that all three had a common code.

The present invention provides a useful visual code to indicate compatibility between mating implant components. While the preferred embodiment comprises a color code, other visual codes could be used in accordance with the invention. For example, symbols with distinct shapes that are readily recognizable could be used in place of or in conjunction with the color codes. It will be understood by those skilled in the art that these and other variations in design and construction may be made to the preferred embodiment without departing from the spirit and scope of the invention defined by the appended claims.

What is claimed is:

1. A coding scheme in combination with femoral, tibial and articular surface components of a prosthetic knee system for communicating the compatibility of the femoral, tibial and articular surface components of the system, the system having a plurality of sizes each of femoral, tibial and articular surface components: each of the components being enclosed in a package, wherein a visual code is placed on the package of a particular size articular surface component and all femoral components which are compatible with the particular size articular surface component have the same visual code placed on their packages as is placed on the package of the articular surface component and all tibial components which are compatible with the particular size articular surface component have the same visual code placed on their packages as is placed on the package of the articular surface component, the implant system having at least one size of the femoral components and tibial components which is marked with more than one visual code thus indicating compatibility of the at least one size of the femoral or tibial component with more than one of the sizes of the articular surface component, whereby compatibility of a selected packaged femoral component, a selected packaged tibial component, and a selected packaged articular surface component is communicated when a common code is on all three packages.

2. A method of verifying the compatibility of femoral, tibial and articular surface components of a prosthetic knee implant system, the method comprising the steps of:

providing a plurality each of femoral, tibial, and articular surface components of a prosthetic knee system;

assigning a unique code to each particular size of articular surface component;

assigning the same code assigned to each particular size articular surface component to each femoral component which is compatible with each particular size articular surface component;

assigning the same code assigned to each particular size articular surface component to each tibial component which is compatible with each particular size articular surface component;

assigning at least one femoral and at least one tibial component more than one code, thus indicating that the at least one femoral and at least one tibial component are compatible with more than one articular surface component;

selecting one each of femoral, tibial and articular surface components and comparing the codes on the three selected components to verify that the three components have a common code among them.

3. A method for selecting prosthetic knee implant system components for compatibility, the method comprising the steps of:

providing a plurality each of femoral, tibial, and articular surface components of a prosthetic knee system;

assigning a unique code to each particular size of articular surface component;

assigning the same code assigned to each particular size articular surface component to each femoral component which is compatible with each particular size articular surface component;

assigning the same code assigned to each particular size articular surface component to each tibial component which is compatible with each particular size articular surface component;

assigning at least one femoral and at least one tibial component more than one code, thus indicating that the at least one femoral and at least one tibial component are compatible with more than one articular surface component;

selecting a femoral component to fit the femur;

selecting a tibial component to fit the tibia;

comparing the codes of the selected femoral and tibial components to identify which codes they have in common; and selecting an articular surface component having a code in common with the selected femoral and tibial components.

4. The method of claim 3 wherein if there is no common code between the selected femoral component and the selected tibial component, one of the femoral component selection and tibial component selection is changed until there is a common code between them.

5. The method of claim 3 wherein after all three components have been selected the codes of all three components are compared to verify that a common code exists among the selected components.

* * * * *